(12) United States Patent
Besso et al.

(10) Patent No.: US 11,471,626 B2
(45) Date of Patent: Oct. 18, 2022

(54) CONTAINERS FOR AEROSOL-GENERATING DEVICES

(71) Applicant: Philip Morris Products S.A., Neuchatel (CH)

(72) Inventors: Clement Besso, Neuchatel (CH); Frederic Ulysse Buehler, Neuchatel (CH); Laurent Lavanant, Evian-les-Bains (FR)

(73) Assignee: Philip Morris Products S.A., Neuchatel (CH)

( * ) Notice: Subject to any disclaimer, the term of this patent is extended or adjusted under 35 U.S.C. 154(b) by 421 days.

(21) Appl. No.: 16/805,409

(22) Filed: Feb. 28, 2020

(65) Prior Publication Data

US 2020/0200381 A1   Jun. 25, 2020

Related U.S. Application Data

(62) Division of application No. 15/547,524, filed as application No. PCT/EP2016/052577 on Feb. 5, 2016, now Pat. No. 11,154,668.

(30) Foreign Application Priority Data

Feb. 6, 2015   (EP) ..................................... 15154224

(51) Int. Cl.
*F22B 1/28*   (2006.01)
*A61M 15/00*   (2006.01)
(Continued)

(52) U.S. Cl.
CPC ............. *A61M 15/06* (2013.01); *A24F 40/30* (2020.01); *A24F 40/42* (2020.01); *A61M 15/009* (2013.01);
(Continued)

(58) Field of Classification Search
CPC .......... A24F 40/10; A24F 40/30; A24F 40/42; A61M 15/06; A61M 15/009; F22B 1/284; B65D 25/02; B65D 65/40
See application file for complete search history.

(56) References Cited

U.S. PATENT DOCUMENTS 3,194,275 A   7/1965 Biggs, Jr. et al.
4,331,491 A   5/1982 Shaw et al.
(Continued)

FOREIGN PATENT DOCUMENTS

CN   1072576 A   6/1993
CN   2204094 Y   8/1995
(Continued)

OTHER PUBLICATIONS

Chinese Office Action dated Jun. 22, 2020 in Chinese Patent Application No. 201680007179.0 (with English translation), 11 pages.
(Continued)

*Primary Examiner* — Dana Ross
*Assistant Examiner* — Kuangyue Chen
(74) *Attorney, Agent, or Firm* — Oblon, McClelland, Maier & Neustadt, L.L.P.

(57) ABSTRACT

A container for an aerosol-generating device is provided, including: a first compartment being sealed and tubular, and including a nicotine source; a second compartment being sealed and tubular, and including a delivery enhancing compound; and a transfer section disposed between the first compartment and the second compartment, at least one of the first compartment and the second compartment including a recessed end, and the transfer section being formed by a recess when one end of the first compartment abuts one end of the second compartment.

7 Claims, 4 Drawing Sheets

Figure 1A:
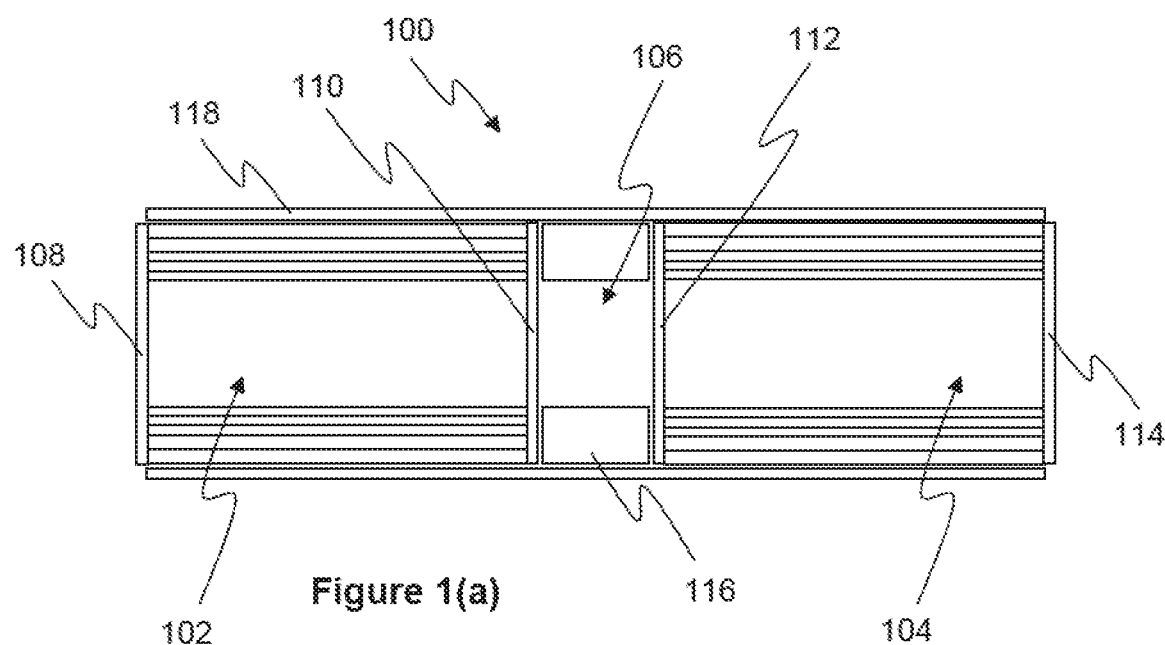

(51) Int. Cl.
  *A61M 15/06* (2006.01)
  *B65D 25/02* (2006.01)
  *B65D 65/40* (2006.01)
  *A24F 40/30* (2020.01)
  *A24F 40/42* (2020.01)
  *A24F 40/10* (2020.01)

(52) U.S. Cl.
  CPC ............. *B65D 25/02* (2013.01); *B65D 65/40* (2013.01); *F22B 1/284* (2013.01); *A24F 40/10* (2020.01)

(56) References Cited

U.S. PATENT DOCUMENTS

| | | | |
|---|---|---|---|
| 4,504,261 | A | 3/1985 | Tanaka |
| 4,813,437 | A | 3/1989 | Ray |
| 2008/0241255 | A1 | 10/2008 | Rose et al. |
| 2012/0204689 | A1 | 8/2012 | Xiu |
| 2014/0060555 | A1 | 3/2014 | Chang et al. |
| 2015/0068542 | A1 | 3/2015 | Chang et al. |
| 2015/0128969 | A1* | 5/2015 | Chapman ................ A24F 40/40 131/329 |
| 2016/0021932 | A1 | 1/2016 | Silvestrini et al. |
| 2016/0022930 | A1 | 1/2016 | Greim et al. |
| 2018/0220713 | A1 | 8/2018 | Chang et al. |
| 2020/0200381 | A1* | 6/2020 | Besso ................ A61M 15/009 |

FOREIGN PATENT DOCUMENTS

| | | |
|---|---|---|
| CN | 2696340 Y | 5/2005 |
| CN | 201294863 Y | 8/2009 |
| CN | 102014995 A | 4/2011 |
| CN | 103202537 A | 7/2013 |
| CN | 103929989 A | 7/2014 |
| CN | 104029884 A | 9/2014 |
| CN | 104188111 A | 12/2014 |
| EP | 0 149 997 A2 | 7/1985 |
| EP | 2 481 308 A1 | 8/2012 |
| GB | 1 013 656 | 12/1965 |
| GB | 1 495 631 | 12/1977 |
| JP | 2010-89821 A | 4/2010 |
| JP | 2010-532672 A | 10/2010 |
| WO | WO 2008/121610 A1 | 10/2008 |
| WO | WO 2014/139611 A1 | 9/2014 |
| WO | WO 2014/140320 A1 | 9/2014 |
| WO | 2014/187763 A1 | 11/2014 |
| WO | WO 2015/000974 A1 | 1/2015 |
| WO | WO-2019171170 A1 * | 9/2019 ............. A61K 31/01 |

OTHER PUBLICATIONS

Japanese Office Action dated Mar. 30, 2020 in Japanese Patent Application No. 2017-539558 (with English translation), 10 pages.
International Search Report and Written Opinion dated Jul. 8, 2016 in PCT/EP2016/052577, filed Feb. 5, 2016.
Extended European Search Report dated Jan. 7, 2020, in Patent Application No. 19202794.4, 9 pages.
Combined Chinese Office Action and Search Report dated Nov. 11, 2019, in Patent Application No. 201680007179.0, 17 pages (with English translation).
Chinese Office Action dated Aug. 5, 2019, in Patent Application No. 201680007179.0, 3 pages (with English translation).
"Make Your Own Kraft Paper Tubes" 2017, 15 pages, www.instructables.com/id/make-your-own-kraft-paper-tubes/.
Chinese Board Opinion dated Nov. 24, 2021 in corresponding Chinese Patent Application No. 201680007179.0 (with English Translation), 15 pages.
"Packaging Materials Science", edited by Liu Xisheng, Jilin University Press, published in Nov. 1997, pp. 251-252, Figs. 11-1.
Chinese Office Action dated Aug. 3, 2021 in corresponding Chinese Patent Application No. 201910990731.8 (with English translation), 18 pages.

* cited by examiner

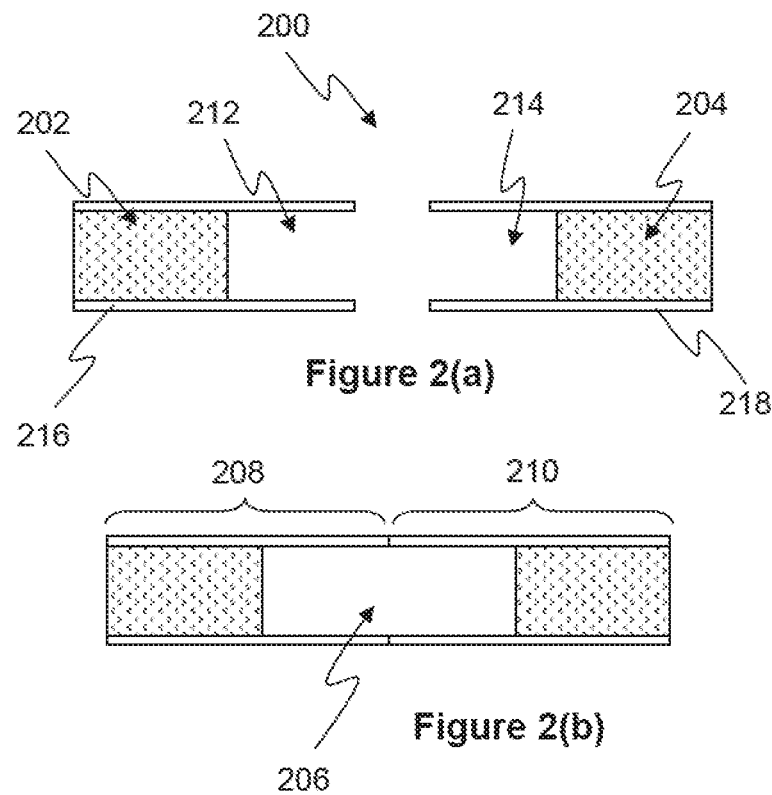
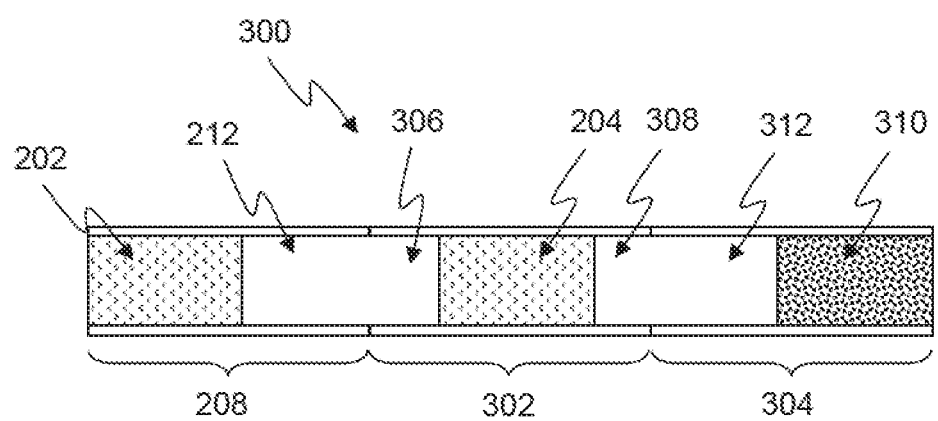

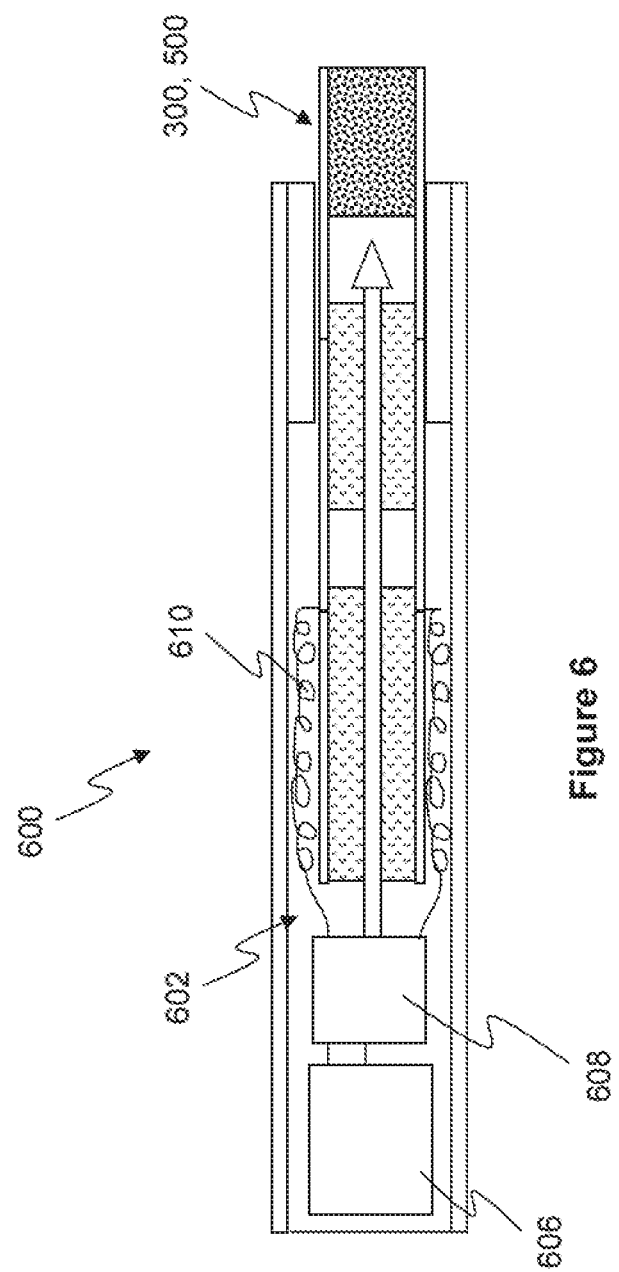

CONTAINERS FOR AEROSOL-GENERATING DEVICES

CROSS-REFERENCE TO RELATED APPLICATIONS

This application is a divisional application of and claims the benefit of priority under 35 U.S.C. § 120 from U.S. application Ser. No. 15/547,524, filed on Jul. 31, 2017, which is a U.S. national stage application under 35 U.S.C. § 371 of PCT/EP2016/052577, filed on Feb. 5, 2016, and claims the benefit of priority under 35 U.S.C. § 119 from EP Application No. 15154224.8, filed on Feb. 6, 2015, the entire contents of each of which are incorporated herein by reference.

The present invention relates to a container for an aerosol-generating device, and to an aerosol-generating device configured to use the container to generate an aerosol. In particular, the invention relates to a container comprising reactants for forming aerosolised particles.

Devices and methods for delivering nicotine or other medicament to a subject in which a delivery enhancing compound is reacted with nicotine or other medicament in the gas phase to form an aerosol of particles are known in the art. For instance, WO 2008/121610 A1 discloses a device in which a delivery enhancing compound and nicotine or other medicament are stored in separate reservoirs. The reactants, that is the delivery enhancing compound and the nicotine or other medicament, form liquid-vapour mixtures in the reservoirs. In use, the respective vapours are brought together to react with one another to form gaseous particles.

In order to improve storage of the liquid reactants, it has been proposed to use aluminium canisters within a disposable article for use in a device. The aluminium canisters are formed into an article by combining them together, generally in a spaced apart relationship, using an outer wrapper. The use of aluminium canisters enables the volatile delivery enhancing compound and the nicotine or other medicament to be stored without substantial degradation by oxidation, hydrolysis or other unwanted reactions, which may alter the properties of the reactants.

However, the use of aluminium canisters increases the cost and complexity of the article, in addition to increasing the manufacturing costs and complexity.

It is therefore an object of the present invention to provide an article for use in an aerosol-generating device which reduces the cost and complexity of an article having aluminium canisters without significantly compromising the improved storage of the liquid reactants provided by such aluminium canisters.

It is a further object of the present invention to reduce the complexity of manufacturing such articles.

According to a first aspect of the present invention, there is provided a container for an aerosol-generating device. The container comprises: a first compartment, being sealed and tubular and comprising a nicotine source; a second compartment, being sealed and tubular and comprising a delivery enhancing compound; and a transfer section arranged between the first compartment and the second compartment. The first compartment and the second compartment are formed from a laminate material, the laminate comprising at least one layer of cardboard material and at least one layer of polymeric material. The layer of polymeric material forms the internal surface of the first compartment and second compartment.

Forming the compartments from such a laminate material may reduce the manufacturing complexity as compared to the prior art compartments formed from aluminium. The use of laminate materials having a base of cardboard also reduces the cost of the compartments, and enables efficient manufacturing techniques for forming cardboard tubes to be used.

In addition, the use of a polymeric material to form the inner surface of the compartments reduces or eliminates any degradation of the nicotine source, and more particularly reduces or eliminates any degradation of the delivery enhancing compound, which may otherwise occur when the aluminium compartments of the prior art act as a catalyst. The use of polymeric material also maintains a good barrier to oxygen, moisture and UV light, all of which may also cause the degradation of the compartment contents.

Preferably, the laminate material further comprises at least one layer of metallic material which is provided adjacent the layer of polymeric material. The metallic layer may improve the barrier to oxygen, moisture and UV light. The metallic layer is preferably formed from aluminium. In addition, where the container is used with an aerosol-generating device having a heater, the heat transfer between the heater and the contents of the compartments may be improved by the provision of the metallic layer.

The at least one layer of polymeric material may comprise a material selected from the group consisting of polypropylene; polyethylene; modified acrylonitrile methyl acrylate copolymer ultra-high molecular weight polyethylene; fluorinated ethylene propylene; polyether ether ketone; liquid crystal polymer, polyoxymethylene; and mixtures thereof. In a particularly preferred embodiment, the polymeric material is a modified acrylonitrile methyl acrylate copolymer, available as Barex®. The use of such materials may enable a film to be formed using standard machinery for processing polymeric materials such as PVC, which are well-known in this field. Furthermore, these materials typically do not degrade, or react with, in any significant way the nicotine source, or delivery enhancing compound.

In one embodiment, at least one layer of the laminate may have embedded therein, at least one of: a plurality of metal particles; at least one metal wire; and at least one metal film. Embedding such materials may enable heating of the container by either electrical conduction, or induction. In this embodiment, the cardboard acts as an insulator to reduce the heating requirements and to reduce the external surface temperature. The interaction between the embedded metal and a device for use with the container is described in detail below.

The first compartment and the second compartment are preferably sealed at each of their ends by a film. The seal is preferably affected by heat-sealing the film to the container, or induction welding. Preferably the film is a thin-film, and is preferably frangible. Any suitable film may be used, but preferably the film comprises metal, more preferably aluminium. The film may be a laminate comprising at least one layer of a polymeric material, and a layer of metal. The polymeric material is preferably provided on the internal surface of the film.

In the first aspect of the present invention, at least one of the first compartment and the second compartment may comprise at least one recessed end, wherein the transfer section is formed by the recess when one end of the first compartment abuts one end of the second compartment.

According to a second aspect of the present invention, there is provided a container for an aerosol-generating device which comprises: a first compartment being sealed and tubular, and comprising a nicotine source; a second compartment being sealed and tubular, and comprising a delivery enhancing compound; and a transfer section arranged between the first compartment and the second compartment. At least one of the first compartment and the second compartment comprises a recessed end, and the transfer section is formed by the recess when one end of the first compartment abuts one end of the second compartment.

Advantageously, providing such a recess may reduce the number of components required to form a container having a transfer section. This may reduce the manufacturing costs and complexity.

As will be appreciated, any feature described with reference to the second aspect of the present invention is also, where appropriate, applicable to the first aspect of the present invention, and vice versa.

According to the first or the second aspect of the invention, the compartments may be connected by an outer wrapper extending over the first compartment and the second compartment at least in a region extending either side of the abutting ends. The outer wrapper may extend substantially along the whole longitudinal length of the container.

As used herein, the term "longitudinal" is used to describe the direction between the downstream or proximal end and the opposed upstream or distal end of the aerosol-generating article or aerosol-generating device and the term "transverse" is used to describe the direction perpendicular to the longitudinal direction.

The other of the first compartment and the second compartment which comprises the at least one recessed end may also comprise at least one recessed end. The recessed end of the first compartment may abut the recessed end of the second compartment to form the transfer section. In this way, a suitable longitudinal length of transfer section can be formed without compromising the structural rigidity of a tubular element forming the recess.

The container may further comprise a further portion, and a further transfer section arranged either between the first compartment and the further portion, or between the second compartment and the further portion. The further portion may be any appropriate function portion, including: a filter portion; a flavour portion; an aerosol-mixing chamber portion; and an aerosol-cooling portion. The flavour portion may comprise tobacco, cast-leaf tobacco, homogenised tobacco, tobacco extract, natural flavours, or artificial flavours. The further transfer section is preferably also formed by at least one recessed end of one of: the first compartment; the second compartment; and the further portion. This may further reduce the number of components required to form the container.

The further portion may comprise a mouthpiece. The mouthpiece may be sealed at the downstream end of the container. The mouthpiece may comprise any suitable material or combination of materials. Examples of suitable materials include thermoplastics that are suitable for food or pharmaceutical applications, for example polypropylene, polyether ether ketone (PEEK) and polyethylene.

The portion of the at least one recessed end is preferably configured to overlay at least a portion of the adjacent compartment. Preferably, the first compartment and the second compartment are affixed to each other. By arranging the compartments in this way, the container can be made without the need for an outer wrapper, which may reduce costs. The nesting of the compartments, with one end of a compartment being received in the recess of the other compartment may be an efficient process for joining such compartments together.

The overlaying portion of the at least one recessed end preferably abuts a neck portion of the adjacent compartment. This may facilitate the nesting. Such a neck portion may enable the longitudinal length of the transfer section to be maintained more easily during manufacture, and better resists any axial loading placed on the container, for example when the container is placed in a device. The neck portion of the adjacent compartment is preferably formed from an outer tube having a length less than the length of the compartment. The outer diameter of the outer tube is preferably substantially the same as the outer diameter of the tubular portion forming the recess.

The overlaying portion of the at least one recessed end is preferably adhered to the adjacent compartment. Preferably the joint between the first compartment and the second compartment is sealed, more preferably the joint is not permeable to air. Any suitable adhesive may be used to join the compartments together. Alternatively, the compartments may be joined together using a heat-sealer.

The compartment having a recess may be formed from a sealed compartment having a first length, and a tubular element having a second length. The second length may be greater than the first length. When a first end of the sealed compartment is adjacent a first end of the tubular element, the tubular element may extend passed the other end of the sealed compartment to form the recess. The first end of the tubular element may be displaced from the first end of the sealed compartment such that a neck portion is formed.

The tubular element may be cardboard or any other suitable material.

The container preferably comprises a first compartment comprising a nicotine source, a second compartment comprising a delivery enhancing compound, two transfer sections, and a filter section. Each of the first compartment, second compartment and filter section may comprise at least one recessed end. The second compartment may comprise two recessed ends. The container may be formed by laying the first compartment, second compartment and filter section in end-to-end abutting relationship, and joining them together, for example with an overwrapper of material. The components may be arranged such that the first compartment is upstream of the second compartment which is upstream of the filter section. The recessed ends may abut to form the transfer sections.

The first compartment may comprise a recessed end, the second compartment may comprise a neck portion and a recessed end, and the filter section may comprise a neck portion. The recessed end of the first compartment may overlay the neck portion of the second compartment to form a first transfer section, and the recessed end of the second compartment may overlay the neck portion of the filter section to form a second transfer section.

As will be appreciated, further compartments, or portions such as a mixing chamber or the like, can be provided by incorporating further recessed ends, and neck portions as required.

As used herein, the terms 'upstream', 'downstream' and 'distal' and 'proximal' are used to describe the relative positions of components, or portions of components, of aerosol-generating articles, aerosol-generating devices and aerosol-generating systems according to the invention in relation to the direction of air drawn through the aerosol-generating articles, aerosol-generating devices and aerosol-generating systems during use thereof.

The upstream and downstream ends of the container are defined with respect to the airflow when a user draws on the proximal or mouth end of the container. Air is drawn into the aerosol-generating article at the distal or upstream end, passes downstream through the aerosol-generating articles and exits the aerosol-generating article at the proximal or downstream end.

The first compartment may comprise a tubular porous element. The nicotine source may be sorbed on the tubular porous element.

The second compartment may comprise a tubular porous element. Preferably, the delivery enhancing compound is sorbed on the tubular porous element.

As used herein, by "sorbed" it is meant that the delivery enhancing compound, or volatile liquid, is adsorbed on the surface of the tubular porous element, or absorbed in the tubular porous element, or both adsorbed on and absorbed in the tubular porous element.

The tubular porous element preferably has a longitudinal length of between about 5 mm and about 20 mm, more preferably of between about 7.5 mm and about 15 mm, and even more preferably the tubular porous element has a longitudinal length of between about 9 mm and about 11 mm or of about 10 mm.

The tubular porous element may be a hollow cylinder. The hollow cylinder is preferably a right circular hollow cylinder.

The second compartment preferably has a longitudinal length of between about 5 mm and about 50 mm, more preferably between about 20 mm and about 40 mm. Preferably the second compartment has a longitudinal length of about 35 mm.

The volume of the first compartment and the second compartment may be the same or different. Preferably, the volume of the first compartment is greater than the volume of the second compartment.

The molar ratio of (nicotine comprised in the first compartment) to (delivery enhancing compound comprised in the second compartment) is preferably comprised between 5:1 to 1:5 and more preferably between 2:1 and 1:2.

The molar ratio of (nicotine comprised in the first compartment) to (organic acid comprised in the second compartment) is preferably comprised between 5:1 to 1:5 and more preferably between 2:1 and 1:2.

The molar ratio of (nicotine comprised in the first compartment) to (lactic acid comprised in the second compartment) is preferably comprised between 5:1 to 1:5 and more preferably between 2:1 and 1:2.

The first compartment comprises a nicotine source. The nicotine source preferably comprises one or more of nicotine, nicotine base, a nicotine salt, or a nicotine derivative.

The nicotine source may comprise natural nicotine or synthetic nicotine. The nicotine source may comprise nicotine base, a nicotine salt, such as nicotine-HCl, nicotine-bitartrate, or nicotine-ditartrate, or a combination thereof.

The first compartment may further comprise an electrolyte forming compound. The electrolyte forming compound may be selected from the group consisting of alkali metal hydroxides, alkali metal oxides, alkaline earth metal oxides, sodium hydroxide (NaOH), calcium hydroxide ($Ca(OH)_2$), potassium hydroxide (KOH) and combinations thereof.

The first compartment may further comprise other components including, but not limited to, tobacco, cast-leaf tobacco, homogenised tobacco, tobacco extract, natural flavours, artificial flavours and antioxidants.

Preferably, the first compartment comprises a liquid nicotine formulation. The liquid nicotine formulation may comprise pure nicotine, a solution of nicotine in an aqueous or non-aqueous solvent or a liquid tobacco extract. The liquid nicotine solution may comprise an aqueous solution of nicotine base, a nicotine salt, such as nicotine-HCl, nicotine-bitartrate, or nicotine-ditartrate and an electrolyte forming compound. The liquid nicotine solution may comprise a non-aqueous solution of nicotine base, a nicotine salt, such as nicotine-HCl, nicotine-bitartrate, or nicotine-ditartrate and an electrolyte forming compound.

In a preferred embodiment, the first compartment comprises a volatile liquid nicotine source.

The second compartment preferably comprises a volatile delivery enhancing compound. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. The volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

The volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid. Preferably, the delivery enhancing compound comprises an acid. More preferably, the delivery enhancing compound comprises an acid having a vapour pressure of at least about 5 Pa at 20° C. Preferably, the acid has a greater vapour pressure than nicotine at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the carboxylic acid comprises a 2-oxo acid, or lactic acid. Preferably, the carboxylic acid comprises lactic acid. Other suitable acid includes aspartic acid, glutamic acid, and salicylic acid.

The 2-oxo acid may comprise an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. The delivery enhancing compound may comprise pyruvic acid.

The tubular porous element is preferably a sorption element with an acid sorbed thereon.

The tubular porous element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Where the second compartment comprises a tubular porous element, the tubular porous element may comprise one or more porous materials selected from the group consisting of porous plastic materials, porous polymer fibres, ceramic fibres, and porous glass fibres. The one or more porous materials may or may not be capillary materials and are preferably inert with respect to the acid. The particular preferred porous material or materials will depend on the physical properties of the acid. The one or more porous materials may have any suitable porosity so as to be used with different acids having different physical properties.

Suitable porous fibrous materials include, but are not limited to: cellulose cotton fibres, non-woven felts, cellulose acetate fibres and bonded polyolefin fibres, such as a mixture of polypropylene and polyethylene fibres.

The tubular porous element may have any suitable size and shape.

The size, shape and composition of the tubular porous element may be chosen to allow a desired amount of volatile delivery enhancing compound to be sorbed on the tubular porous element.

The tubular porous element advantageously acts as a reservoir for the delivery enhancing compound.

The compartments of the container may be formed by any suitable known method for forming tubes from sheet material, in particular methods for forming tubes from paper-based sheet material. For example, the tubes for the compartments may be formed by helically winding elongate laminate material onto a mandrel, the edges of the elongate laminate material abutting each other. Alternatively, the laminate material may be formed by winding consecutive layers of the laminate onto the mandrel to build up the compartment and laminate material simultaneously.

In an alternative example, the laminate, or layers thereof, are wound around a mandrel such that a seam is formed parallel to the longitudinal axis of the mandrel.

The first example is preferred as it enables a tube to be formed of substantially infinite length.

According to a further aspect of the present invention, there is provided an aerosol-generating system. The system comprises: a container as described herein; and an aerosol-generating device configured to receive the container. The device comprises: a piercing member for piercing each of the first compartment and the second compartment of the container.

As used herein, the term "aerosol-generating device" refers to an aerosol-generating device that interacts with an aerosol-generating article, in this case a container as described herein, to generate an aerosol that is directly inhalable into a user's lungs thorough the user's mouth.

The aerosol-generating device preferably comprises heating means for heating one or both of the nicotine source and the volatile delivery enhancing compound source of the container. The aerosol-generating device may comprise one heating means for heating both the nicotine source and the volatile delivery enhancing compound source. The aerosol-generating device may comprise at least two heating means. The nicotine source and the volatile delivery enhancing compound source may be heated at identical or different temperatures.

The compartments of the container may be arranged in parallel. The compartments of the container are preferably arranged in series. As used herein, by "series" it is meant that the first compartment and the second compartment are arranged within the container so that in use an air stream drawn through the container passes through the first compartment and then passes through the second compartment. Nicotine vapour is released from the nicotine source in the first compartment into the air stream drawn through the container and delivery enhancing compound vapour is released from the delivery enhancing compound in the second compartment. The delivery enhancing compound vapour reacts with the nicotine vapour in the gas phase to form an aerosol, which is delivered to a user.

The aerosol-generating device preferably has at least one air inlet. As used herein, the term "air inlet" is used to describe one or more apertures through which air may be drawn into the aerosol-generating system.

As used herein, the term "air outlet" is used to describe one or more aperture through which air may be drawn out of the aerosol-generating system. Preferably, the air outlet is provided at the downstream end of the container.

Preferably, each of the first compartment and the second compartment comprises a frangible barrier at each end. The frangible barrier is configured such that the barrier can be pierced by the piercing member when the container is inserted into the aerosol-generating device by the user.

Preferably the outer housing of the aerosol-generating device comprises a cavity configured to receive the container. Preferably, the cavity has a longitudinal length greater than the longitudinal length of the elongate piercing member. In this way, the piercing portion of the piercing member is not exposed, or accessible by the user.

Preferably, the cavity of the aerosol-generating device is substantially cylindrical. The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the container to be received in the cavity.

The aerosol-generating system may further comprise a power supply for providing power to the, when present, at least one heater, and control circuitry. The control circuitry is preferably configured to control the supply of power to the at least one heater such that the delivery enhancing compound and the nicotine source are sufficiently volatilised to enable the generation of an aerosol.

As described above, the material forming the compartments may comprise a plurality of metal particles, at least one metal wire, or at least one metal film. In this embodiment, the at least one heater may utilise the embedded metal to form at least part of the heater. In this case, the device comprises means for interacting with the embedded metal to cause the temperature of the container to increase. The interaction may be via induction, in which case the device comprises an inductive coil to couple with the embedded metal. The interaction may be via electrical conduction, in which case the device comprises electrical contacts for engaging with corresponding electrical contacts provided on the container.

In use, the nicotine may react with the acid in the gas phase, either in a transfer section or in the second compartment to form aerosolised nicotine salt particles.

It will be understood that the aerosol-generating system may also be regarded as an aerosol delivery system. That is to say, the aerosol-generating system provides means for the nicotine source, such as a nicotine formulation, and the delivery enhancing compound, such as a pyruvic acid or lactic acid, to mix and generate an aerosol but does not actively generate the aerosol.

Where the container comprises a filter section, the filter section may comprise a filtration material capable of removing at least a portion of any unreacted acid mixed with aerosolised nicotine salt particles drawn through the filter section. The filtration material may comprise a sorbent, such as activated carbon.

As will be appreciated, a number of factors influence the formation of the nicotine salt particles. In general, in order to control the nicotine delivery it is important to control the vaporisation of the nicotine formulation and the acid. It is also important to control the relative quantities of the nicotine and the acid. Preferably, the molar ratio of acid to nicotine in the aerosol forming chamber is about between about 5:1 and about 1:5, preferably between about 2:1 and about 1:2, preferably about 1:1. The use of acid as a delivery enhancing compound has been found to approximately double the delivery rate of nicotine to a user for equivalent power supplied to the vaporiser.

The vaporisation of the acid may be controlled by the concentration of the acid in the first compartment, and by the exchange surface area of acid in the second compartment. The vaporisation of the acid may be controlled by heating the second compartment of the container or by heating ambient air drawn through the device before it passes through the second compartment.

The container is preferably substantially cylindrical in shape. The container may have a transverse cross-section of any suitable shape. Preferably, the container is of substantially circular transverse cross-section or of substantially elliptical transverse cross-section. More preferably, the container is of substantially circular transverse cross-section.

Preferably, the container has a transverse cross-section substantially the same shape as the cavity of the aerosol-generating device.

The container may simulate the shape and dimensions of a tobacco smoking article, such as a cigarette, a cigar, a cigarillo or a pipe, or a cigarette pack. Preferably, the housing simulates the shape and dimensions of a cigarette.

The aerosol-generating device and container may be arranged to releasably lock together when engaged.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol-generating system and device are preferably portable. The aerosol-generating system may have a size and shape comparable to a conventional smoking article, such as a cigar or cigarette.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

Figure 1B:
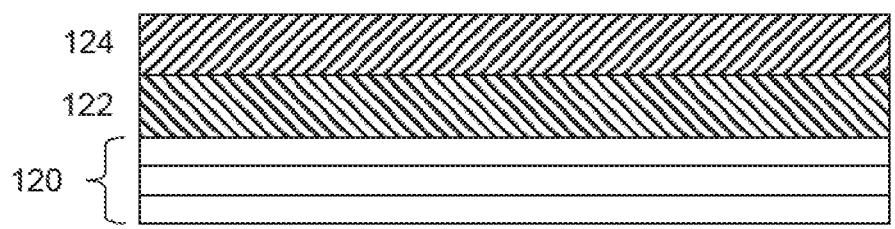
Figure 4A:
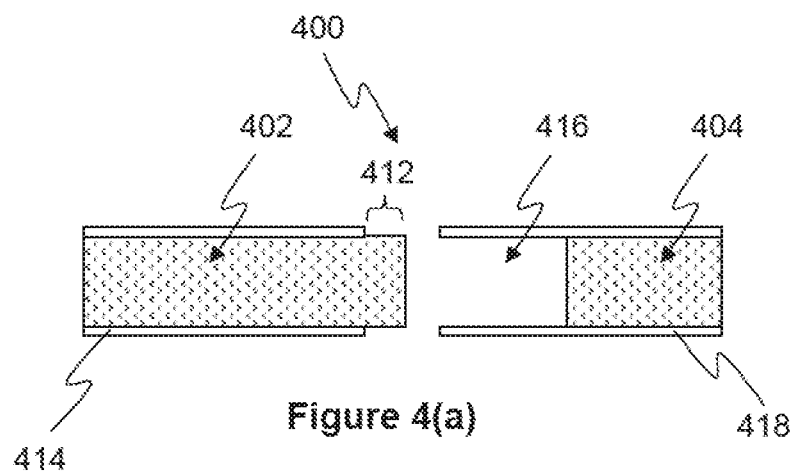
Figure 4B:
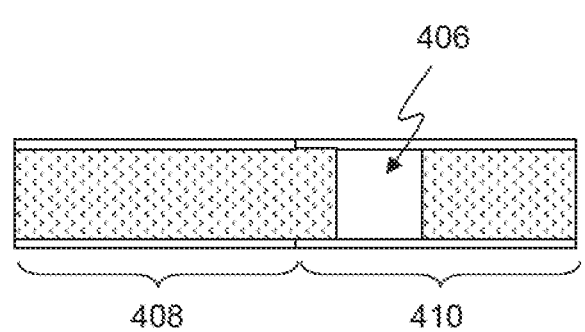
Figure 5:
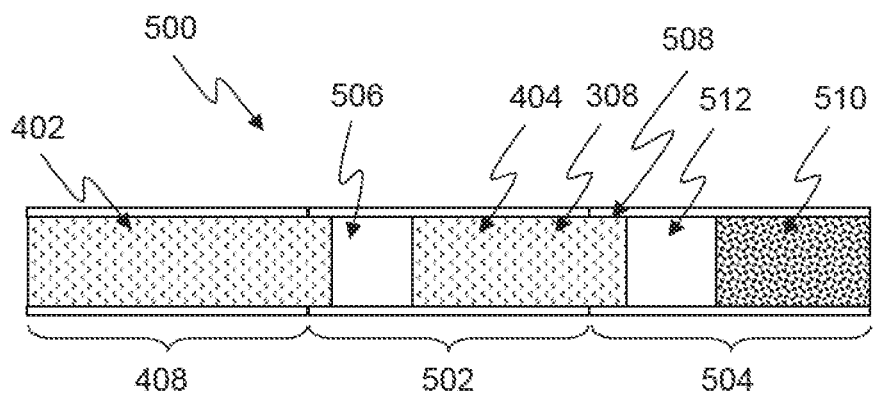

The invention will be further described, by way of example only, with reference to the accompanying drawings in which:

FIGS. 1(a) and 1(b) show a cross-sectional view of a container according to one embodiment of the present invention and a cross-section of the material used to form the container;

FIGS. 2(a) and 2(b) show a schematic representation of a container according to a further embodiment of the present invention:

FIG. 3 shows a schematic representation of a further example of a container according to the embodiment of the present invention shown in FIGS. 2(a) and 2(b);

FIGS. 4(a) and 4(b) show a schematic representation of a container according to a yet further embodiment of the present invention;

FIG. 5 shows a schematic representation of a further example of a container according to the embodiment of the present invention shown in FIGS. 4(a) and 4(b); and FIG. 6 shows a schematic representation of an aerosol-generating system according to one embodiment of the present invention.

FIG. 1(a) shows a cross-sectional view of a container 100 for use in an aerosol-generating device. The container 100 comprises a first compartment 102, a second compartment 104 and a transfer section 106. The first compartment comprises a nicotine source, and in particular a volatile liquid nicotine source. The second compartment comprises a delivery enhancing compound, in particular a volatile liquid delivery enhancing compound comprising an organic acid such as lactic acid or pyruvic acid. The transfer section 106 is a hollow tubular element provided between the first compartment and the second compartment.

The first compartment and the second compartment are formed from hollow tubes, and are sealed at each end by frangible barriers 108, 110 and 112, 114 respectively. The transfer section 106 is also formed from a hollow tube 116, the tube abutting an end of each compartment. The first compartment 102, second compartment 104 and transfer section 106 are combined together by an outer wrapper 118.

FIG. 1(*b*) shows a cross-section of the laminate material used to form hollow tubular elements of the first compartment and second compartment. In this example, the laminate material comprises three layers of paper 120, a layer of metal 122, and a layer of a polymeric material 124. In forming the tubular elements for the first compartment and the second compartment, the laminate is arranged such that the layer of polymeric material forms the inner surface of the compartments. In this example, the layer of metal is aluminium, and the layer of polymeric material is a modified acrylonitrile methyl acrylate copolymer, available commercially as Barex®.

Forming the compartments from such a laminate material reduces the manufacturing complexity as compared to the prior art method of forming them from extruded aluminium. The use of laminate materials having a base of paper also reduces the cost of the compartments, and enables known, and efficient manufacturing techniques for forming cardboard tubes to be used.

The polymeric material used to form the inner surface of the compartments reduces or eliminates any degradation of the nicotine source, and more particularly reduces or eliminates any degradation of the pyruvic or lactic acid, which may otherwise occur when the aluminium compartments of the prior art act as a catalyser. The use of polymeric material also maintains a good barrier to oxygen, moisture and UV light, all of which may also cause the degradation of the compartment contents.

The frangible barriers 108, 110, 112, and 114 are heat-sealed to the end faces of the respective compartments. The frangible barriers are also formed from a laminate material. The frangible barrier laminate comprises a layer of polymeric material and a layer of metal. Similarly to the laminate material used to form the hollow tubular elements of the compartments the polymeric material is provided on the inner surface of the barrier. Again, in this example, the polymeric material is a modified acrylonitrile methyl acrylate copolymer, and the metal is aluminium.

The tubular elements of the first compartment 102 and the second compartment 104 may be formed by any suitable known method for forming tubes from sheet material, in particular methods for forming tubes from paper-based sheet material. Indeed, at least one advantage of the container is that it may be formed using known methods which are less complex and cheaper than the methods for forming the metal containers of the prior art.

In one example, the tubular elements are formed by helically winding elongate laminate material onto a mandrel, the long edges of the elongate laminate material abutting each other. In this way, a hollow tube may be formed of infinite length. Once the tube is formed it is cut to the required lengths for the first compartments and second compartments. The laminate material may be formed by winding consecutive layers of the laminate onto the mandrel to build up the tubular element and laminate material simultaneously.

FIGS. 2(*a*) and 2(*b*) show a schematic representation of another example of a container 200. Similarly to the container described with reference to FIGS. 1(*a*) and 1(*b*), the container 200 comprises a first compartment 202 comprising a nicotine source, a second compartment 204 comprising a delivery enhancing compound, and a transfer section 206. Again, each compartment is sealed by a frangible barrier (not shown) at each end of a hollow tubular element. Each compartment may be formed in a similar manner, using similar materials, to the compartments described above with reference to FIGS. 1. Alternatively, other known methods and materials, such as extruded aluminium canisters can be used to form the compartments.

As can be seen, the container is formed from two sections 208 and 210, each section comprising a compartment and a recess 212, 214 respectively. The recess 212, 214 is formed from an outer wrapper 216, 218 of material, such as paper, extending passed one end of the compartment. The transfer section is formed by abutting the first section to the second section, the recesses 212 and 214 being combined to form the transfer section 206. The two sections are either directly adhered to each other, or a further outer wrapper of material is provided at least over the region extending either side of the join between the two sections.

Such an arrangement reduces the number of components required to form a container having a transfer section between compartments.

Another example of an embodiment of the container shown in FIG. 2(*b*) is shown in FIG. 3. In this example, the container comprises a first section 208, which is the same as the first section described above with reference to FIG. 2, a second section 302, and a third section 304. The section 302 including the second compartment 204 is provided with recesses 306 and 308 at each end. The recesses are formed in the same way as described above. The third section 304 comprises a filter 310 and a recess 312. The filter 310 may be any appropriate filter for use in a smoking article, such as a tow filter. The recess 202 of the first section 208 abuts the recess 306 of the second section 302 to form a first transfer section. The recess 306 of the second section 302 abuts the recess 312 of the third section 304 to form a second transfer section. Again the sections are either directly adhered to each other, or a further outer wrapper of material is provided at least over the region extending either side of the join between the each of the sections.

FIGS. 4(*a*) and 4(*b*) show a schematic representation of another example of a container 400. Similarly to the container described with reference to FIGS. 1(*a*) and 1(*b*), the container 400 comprises a first compartment 402 comprising a nicotine source, a second compartment 404 comprising a delivery enhancing compound, and a transfer section 406. Again, each compartment is sealed by a frangible barrier (not shown) at each end of a hollow tubular element. Each compartment may be formed in a similar manner, using similar materials, to the compartments described above with reference to FIG. 1. Alternatively, other known methods and materials, such as extruded aluminium canisters can be used to form the compartments.

As can be seen, the container is formed from two sections 408 and 410. The section 408 comprises the first compartment 402, and has a neck portion 412. The neck portion 412 is formed by an outer wrapper 414 not extending along the entire longitudinal length of the compartment 402. The section 410 comprises the second compartment 404, and a recess 416 which is formed from an outer wrapper 418 of material, such as paper, extending passed one end of the compartment. The transfer section is formed from a portion of the recess 416 when the section 408 is engaged with the section 410. As can be seen in FIG. 4(*b*), the recess 416 receives the neck portion 412 of the first compartment 402. The end surface of the outer wrapper 418 abuts the end surface of the outer wrapper 414 to maintain the longitudinal length of the container. The outer wrapper 418 is adhered to the neck portion 412. Such an arrangement reduces the number of components required to form a container having a transfer section between compartments.

Another example of an embodiment of the container shown in FIG. 4(b) is shown in FIG. 5. In this example, the container 500 comprises a first section 408, which is the same as the first section described above with reference to FIG. 4, a second section 502, and a third section 504. The section 502 including the second compartment 404 is provided with a recess 506 at a first end, and a neck portion 508 at a second end. The recess and neck portion are formed in the same way as described above. The third section 504 comprises a filter 510 and a recess 512. The filter 510 may be any appropriate filter for use in a smoking article, such as a tow filter. The recess 506 of the second section 502 engages with the neck portion of the first section 408 to form a first transfer section. The recess 512 of the third section 504 engages with the neck portion of the second section 502 to form a second transfer section.

FIG. 6 shows a cross-sectional view of an aerosol-generating system 600. The system 600 comprises an aerosol-generating device 602 and a container 300, 500 as described above. The aerosol-generating device 602 comprises an outer housing having an elongate cylindrical cavity configured to receive the container 300, 500. The longitudinal length of the cavity is less than the length of the container such that the proximal, or downstream, end of the container 300, 500 protrudes from the cavity.

The device 602 further comprises a piercing member 604. The piercing member is positioned centrally within the cavity of the aerosol-generating device and extends along the longitudinal axis of the cavity. At one end, the piercing member comprises a piercing portion in the form of a cone having a circular base. The piercing member further comprises a shaft portion. As can be seen, when the container is received within the aerosol-generating device, the piercing member is configured to pierce the frangible barriers the first compartment and second compartment.

Air inlets (not shown) are provided at the upstream end of the aerosol-generating device 602. Air outlets (not shown) are provided at the proximal, downstream, filter end of the container 300, 500.

In use, the user applies a longitudinal force to the container to insert it into the aerosol-generating device and pierce the frangible barriers with the piercing member 604. The piercing member 604 breaks the frangible barriers the first compartment and second compartment and creates holes in the seals having a diameter approximately equal to the maximum diameter of the piercing portion. The maximum diameter of the piercing portion is the diameter of the base circle of the cone which forms the piercing portion.

As such, an airflow pathway is created extending from the air inlet (not shown) around the shaft of the piercing member 604, through the first compartment, through the transfer section, through the second compartment, through the second transfer section, exiting through the filter section.

In use, the volatile liquid nicotine vapour released from the volatile liquid nicotine source is entrained into the airflow as it passes through the first compartment. The air then continues through the transfer section, and then through the second compartment where the volatile delivery enhancing compound is entrained into the air flow as the user draws on the downstream end of the container.

The delivery enhancing compound vapour reacts with the nicotine vapour in the gas phase to form an aerosol, which is delivered to the user through the proximal, downstream, end of the container 300, 500.

The aerosol-generating device 602 further comprises a power supply 606, control circuitry 608, and an electrical heater 610. The control circuitry 608 is configured to control the supply of power from the power supply 606 to the electrical heater 610. The electrical heater 610 is shown adjacent the first compartment, and is used to increase the temperature of the volatile liquid nicotine source to volatilize the nicotine at a rate such that the molar ratio of the nicotine vapour and the delivery enhancing compound vapour ensures a substantially complete reaction. In one example, the molar ratio between the nicotine and the delivery enhancing compound where the delivery enhancing compound is lactic acid, is between 5:1 and 1:5, preferably between 2:1 and 1:2, preferably 1:1.

Alternatively, or in addition, an electrical heater may be provided adjacent the second compartment. The control circuitry may be configured to heat the second compartment to a different temperature to the first compartment.

The invention claimed is:

1. A container for an aerosol-generating device, comprising:
    a first compartment being sealed and tubular, and comprising a nicotine source;
    a second compartment being sealed and tubular, and comprising a delivery enhancing compound; and
    a transfer section disposed between the first compartment and the second compartment,
    wherein at least one of the first compartment and the second compartment comprises a recessed end, and
    wherein the transfer section is formed by a recess when one end of the first compartment abuts one end of the second compartment.

2. The container according to claim 1, further comprising a further portion; and a further transfer section disposed either between the first compartment and the further portion or between the second compartment and the further portion.

3. The container according to claim 2, wherein the further transfer section is formed by at least one recessed end of one of: the first compartment, the second compartment, and the further portion.

4. The container according to claim 1, wherein a portion of the recessed end is configured to overlay at least a portion of an adjacent compartment.

5. The container according to claim 4, wherein the portion of the recessed end overlays said portion of the adjacent compartment and abuts a neck portion of the adjacent compartment.

6. The container according to claim 4, wherein the portion of the recessed end overlays said portion of the adjacent compartment is adhered to the adjacent compartment.

7. The container according to claim 1, wherein the first compartment and the second compartment are affixed to each other.

* * * * *